US012746279B2

(12) United States Patent
Andreotti E Silva

(10) Patent No.: US 12,746,279 B2
(45) Date of Patent: Sep. 29, 2026

(54) PEPTIDE COMBINATION, CHIMERIC PEPTIDE, IMMUNOGENIC COMPOSITION, USE OF THE PEPTIDE COMBINATION, USE OF THE CHIMERIC PEPTIDE, USE OF A COMPOSITION, METHOD FOR INDUCING AN IMMUNE RESPONSE AND KIT

(71) Applicants: BIOTICK PESQUISA E DESENVOLVIMENTO TECNOLOGICO LTDA., São Paulo (BR); EMPRESA BRASILEIRA DE PESQUISA AGROPECUARIA-EMBRAPA, Brasília (BR)

(72) Inventor: Renato Andreotti E Silva, Brasília (BR)

(73) Assignees: BIOTICK PESQUISA E DESENVOLVIMENTO TECNOLOGICO LTDA., São Paulo (BR); EMPRESA BRASILEIRA DE PESQUISA AGROPECUARIA—EMBRAPA, Brasília-DF (BR)

( * ) Notice: Subject to any disclaimer, the term of this patent is extended or adjusted under 35 U.S.C. 154(b) by 389 days.

(21) Appl. No.: 18/282,435

(22) PCT Filed: Mar. 15, 2022

(86) PCT No.: PCT/BR2022/050087

§ 371 (c)(1),
(2) Date: Sep. 15, 2023

(87) PCT Pub. No.: WO2022/192974

PCT Pub. Date: Sep. 22, 2022

(65) Prior Publication Data

US 2024/0156925 A1 May 16, 2024

(30) Foreign Application Priority Data

Mar. 16, 2021 (BR) ...................... 10 2021 004904 9

(51) Int. Cl.
*A61K 39/00* (2006.01)

(52) U.S. Cl.
CPC .......... *A61K 39/0003* (2013.01); *A61K 39/00* (2013.01); *C07K 2319/00* (2013.01)

(58) Field of Classification Search
CPC .......... C07K 14/43577; C07K 2319/00; A61K 39/00; A61K 2039/552
See application file for complete search history.

(56) References Cited

PUBLICATIONS

Jia et al., Cell, 2020; 182: 1328-1340 (Year: 2020).*
International Search Report and Written Opinion issued on May 25, 2022 for corresponding PCT Application No. PCT/BR2022/050087, written opinion not translated.
Giachetto, P. F. et al.; "Gene Expression in the Salivary Gland of Rhipicephalus (Boophilus) microplus Fed on Tick-Susceptible and Tick-Resistant Hosts," Frontiers in Cellular and Infection Microbiology, vol. 9, Article 477, 2020, pp. 1-15.
Andreotti, R. et al.; "Advances in tick vaccinology in Brazil: from gene expression to immunoprotection," Frontiers in Bioscience, vol. 10, No. 1, 2018, pp. 127-142.
Aguirre, A. A. R. et al.; "Design of the ATAQ peptide and its evaluation as an immunogen to develop a Rhipicephalus vaccine," Veterinary Parasitology, vol. 221, 2016, pp. 30-38.
Csordas, B. G. et al.; "Molecular characterization of the recombinant protein RmLTI-BmCG-LTB: Protective immunity against Rhipicephalus (Boophilus) microplus," PLoS One, vol. 13, No. 2, 2018, pp. 1-14.

* cited by examiner

*Primary Examiner* — Brian Gangle
*Assistant Examiner* — Lakia J Jackson-Tongue
(74) *Attorney, Agent, or Firm* — POLSINELLI PC

(57) ABSTRACT

The present invention is applied to the field of Biotechnology and Immunology and refers to combinations of immunogenic peptides, chimeric peptides, compositions that comprise them and the uses thereof for control of ticks, particularly ticks of the species *Rhipicephalus microplus*. The present invention further provides kits containing the combinations, chimeric peptides and/or compositions comprising the combinations of immunogenic peptides, and a method for inducing immune response in animals, particularly bovines.

17 Claims, 3 Drawing Sheets

Specification includes a Sequence Listing.

SEQUENCE LISTING

```
<160> NUMBER OF SEQ ID NOS: 12

<210> SEQ ID NO 1
<211> LENGTH: 30
<212> TYPE: PRT
<213> ORGANISM: Rhipicephalus microplus
<220> FEATURE:
<221> NAME/KEY: PEPTIDE
<222> LOCATION: (1)..(11)
<223> OTHER INFORMATION: 73% identity with "insect cuticle protein" of
      I. scapularis
<220> FEATURE:
<221> NAME/KEY: PEPTIDE
<222> LOCATION: (12)..(16)
<223> OTHER INFORMATION: Linker
<220> FEATURE:
<221> NAME/KEY: PEPTIDE
<222> LOCATION: (17)..(30)
<223> OTHER INFORMATION: peptide epitope of Clostridium tetani tetanus
      toxin

<400> SEQUENCE: 1

Thr Asn Glu Pro Gly Thr Ala Pro Gly Glu Thr Gly Pro Gly Pro Gly
1               5                   10                  15

Gln Tyr Ile Lys Ala Asn Ser Lys Phe Ile Gly Ile Thr Glu
            20                  25                  30


<210> SEQ ID NO 2
<211> LENGTH: 48
<212> TYPE: PRT
<213> ORGANISM: Rhipicephalus microplus
<220> FEATURE:
<221> NAME/KEY: PEPTIDE
<222> LOCATION: (1)..(12)
<223> OTHER INFORMATION: 67% identity with "insect cuticle protein" of
      I. scapularis.
<220> FEATURE:
<221> NAME/KEY: PEPTIDE
```

<222> LOCATION: (13)..(17)
<223> OTHER INFORMATION: Linker
<220> FEATURE:
<221> NAME/KEY: PEPTIDE
<222> LOCATION: (18)..(34)
<223> OTHER INFORMATION: 67% identity with “insect cuticle protein” of I. scapularis.
<220> FEATURE:
<221> NAME/KEY: PEPTIDE
<222> LOCATION: (35)..(39)
<223> OTHER INFORMATION: Linker
<220> FEATURE:
<221> NAME/KEY: PEPTIDE
<222> LOCATION: (40)..(48)
<223> OTHER INFORMATION: 67% identity with “insect cuticle protein” of I. scapularis.

<400> SEQUENCE: 2

```
Val Ala Pro Thr Ala Asn Pro Ser Pro Ala Pro Trp Gly Pro Gly Pro
1               5                   10                  15

Gly Gln Ser Pro Val Ala Pro Gly Ala Tyr Asn Pro Pro Ala Pro Ala
            20                  25                  30

Thr Tyr Gly Pro Gly Pro Gly Asn Gln Ser Pro Gln Pro Gln Pro Ala
        35                  40                  45
```

<210> SEQ ID NO 3
<211> LENGTH: 29
<212> TYPE: PRT
<213> ORGANISM: Rhipicephalus microplus
<220> FEATURE:
<221> NAME/KEY: PEPTIDE
<222> LOCATION: (1)..(29)
<223> OTHER INFORMATION: 88% identity with “Chitin binding protein/embryo” of I. scapularis.

<400> SEQUENCE: 3

```
Pro Ala Ser Val Thr Pro Pro Pro Pro Arg Gln Thr Ala Ser Gly Pro
1               5                   10                  15

Gly Pro Gly Gly Pro Pro Ser Ser Gln Thr Pro Arg Ala
            20                  25
```

<210> SEQ ID NO 4
<211> LENGTH: 19
<212> TYPE: PRT
<213> ORGANISM: Rhipicephalus microplus
<220> FEATURE:
<221> NAME/KEY: PEPTIDE
<222> LOCATION: (1)..(19)
<223> OTHER INFORMATION: 70% identity with “Embryonated eggs protein” of I. scapularis.

<400> SEQUENCE: 4

```
Ala Thr Gln Gln Gly Asn Glu Gly Gln Gln Gly Ser Ser Asp Lys Gly
1               5                   10                  15

Gln Glu Leu
```

<210> SEQ ID NO 5
<211> LENGTH: 12
<212> TYPE: PRT
<213> ORGANISM: Rhipicephalus microplus
<220> FEATURE:
<221> NAME/KEY: PEPTIDE
<222> LOCATION: (1)..(12)
<223> OTHER INFORMATION: 55% identity with “Embryonated eggs protein” of I. scapularis.

<400> SEQUENCE: 5

```
Ala Val Asp Pro Ser Ser Pro Glu Gln His Pro Glu
```

```
1               5                   10


<210> SEQ ID NO 6
<211> LENGTH: 22
<212> TYPE: PRT
<213> ORGANISM: Rhipicephalus microplus
<220> FEATURE:
<221> NAME/KEY: PEPTIDE
<222> LOCATION: (1)..(21)
<223> OTHER INFORMATION: 90% identity with "TPR Repetition (Signal
      transduction mechanisms)" of I. scapularis

<400> SEQUENCE: 6

Val Gly Gly Asp Gly Pro Ala Pro Ala Lys His Arg Ser Gly Asp Ser
1               5                   10                  15

Gly Glu Gly Val Asp Asp
            20


<210> SEQ ID NO 7
<211> LENGTH: 33
<212> TYPE: PRT
<213> ORGANISM: Rhipicephalus microplus
<220> FEATURE:
<221> NAME/KEY: PEPTIDE
<222> LOCATION: (1)..(14)
<223> OTHER INFORMATION: 30% identity with "Zinc-dependent
      metalloprotease" of R. microplus
<220> FEATURE:
<221> NAME/KEY: PEPTIDE
<222> LOCATION: (15)..(19)
<223> OTHER INFORMATION: Linker
<220> FEATURE:
<221> NAME/KEY: PEPTIDE
<222> LOCATION: (20)..(33)
<223> OTHER INFORMATION: peptide epitope of Clostridium tetani tetanus
      toxin

<400> SEQUENCE: 7

Glu Asp His Gly Arg Arg Thr Glu Asp Pro Glu Pro Asp Cys Gly Pro
1               5                   10                  15

Gly Pro Gly Gln Tyr Ile Lys Ala Asn Ser Lys Phe Ile Gly Ile Thr
            20                  25                  30

Glu


<210> SEQ ID NO 8
<211> LENGTH: 20
<212> TYPE: PRT
<213> ORGANISM: Rhipicephalus microplus
<220> FEATURE:
<221> NAME/KEY: PEPTIDE
<222> LOCATION: (1)..(20)
<223> OTHER INFORMATION: 45% identity with "Kazal-type serine protease
      inhibitor proteins" of I. scapularis.

<400> SEQUENCE: 8

Pro Val Glu Asp Glu Asp Lys Asp Ser Gln Glu Thr Gln Glu Pro Gly
1               5                   10                  15

Gly Pro Trp Ser
            20


<210> SEQ ID NO 9
<211> LENGTH: 16
<212> TYPE: PRT
<213> ORGANISM: Rhipicephalus microplus
<220> FEATURE:
<221> NAME/KEY: PEPTIDE
<222> LOCATION: (1)..(16)
<223> OTHER INFORMATION: 67% identity with  "Insect cuticle protein -
```

```
      chitin bond" of I. scapularis.

<400> SEQUENCE: 9

Thr Asn Glu Pro Gly Thr Ala Pro Gly Ala Thr Gly Asp Ala Gln Tyr
1               5                   10                  15


<210> SEQ ID NO 10
<211> LENGTH: 21
<212> TYPE: PRT
<213> ORGANISM: Rhipicephalus microplus
<220> FEATURE:
<221> NAME/KEY: PEPTIDE
<222> LOCATION: (1)..(21)
<223> OTHER INFORMATION: 43% identity with "Kunitz / Trypsin inhibitor
      domain" of R. microplus.

<400> SEQUENCE: 10

Phe Pro Pro Tyr Gln Gly Arg Pro Gly Ala Thr Asn Glu Trp Pro Gly
1               5                   10                  15

Ser Pro Tyr Ser Pro
            20


<210> SEQ ID NO 11
<211> LENGTH: 24
<212> TYPE: PRT
<213> ORGANISM: Rhipicephalus microplus
<220> FEATURE:
<221> NAME/KEY: PEPTIDE
<222> LOCATION: (1)..(24)
<223> OTHER INFORMATION: 43% identity with "trypsin inhibitor(BPTI)
      Kunitz" of R. microplus.

<400> SEQUENCE: 11

Thr Lys Pro Ser Pro Pro Ser Gln Glu Ala Pro Ser Ser Thr Asp Glu
1               5                   10                  15

Gly Trp Tyr Pro Pro Arg Arg Arg
            20


<210> SEQ ID NO 12
<211> LENGTH: 12
<212> TYPE: PRT
<213> ORGANISM: Rhipicephalus microplus
<220> FEATURE:
<221> NAME/KEY: PEPTIDE
<222> LOCATION: (1)..(10)
<223> OTHER INFORMATION: 35% identity with "Saliva molecules that
      modulate host response" of I. scapularis.

<400> SEQUENCE: 12

Asp Phe Asp Asp Ser Pro Ser Asp Glu His Thr Gly
1               5                   10
```

PEPTIDE COMBINATION, CHIMERIC PEPTIDE, IMMUNOGENIC COMPOSITION, USE OF THE PEPTIDE COMBINATION, USE OF THE CHIMERIC PEPTIDE, USE OF A COMPOSITION, METHOD FOR INDUCING AN IMMUNE RESPONSE AND KIT

CROSS-REFERENCE TO RELATED APPLICATIONS

This application is a national stage application (under 35 U.S.C. § 371) of PCT/BR2022/050087, filed Mar. 15, 2022, which claims benefit of Brazilian Application No. BR 10 2021 004904 9, filed Mar. 16, 2021, which are incorporated herein by reference in their entireties.

FIELD OF THE INVENTION

The present invention relates to the field of Biotechnology and Immunology. More specifically, the invention approaches the combinations of immunogenic peptides against mammal ticks, chimeric peptides, compositions that comprise them and the uses thereof.

The present invention further provides kits and a method of inducing immune response in mammal animals, particularly bovine.

BACKGROUND OF THE INVENTION

Tick infestation can cause several problems in mammals, particularly for bovine cattle, affecting the health of the animals and reducing the production and quality of meat and milk.

As described by Blecha et al. (BLECHA, I. M. Z. et al. Analysis of Bm86 conserved epitopes: is a global vaccine against Cattle Tick *Rhipicephalus microplus* possible? Braz. J. Vet. Parasitol., Jaboticabal, v. 27, n. 3, p. 267-279 (2018), the tick *Rhipicephalus* (*Boophilus*) *microplus* is responsible for several losses in agribusiness, thus the control thereof is made mainly by means of chemical acaricides, which results in the contamination of products of animal origin and of the environment, apart from the fact that, the reports on the fact that the ticks appear to develop resistance to said acaricides become more and more frequent.

The resistance to several classes of acaricides is a problem that has been increasingly observed and reported, making researchers seek alternative measures for the control of tick infestation in bovines (AGUIRRE, A. A. R. et al. Design of the ATAQ peptide and its evaluation as an immunogen to develop a *Rhipicephalus* vaccine. Veterinary Parasitology. 221 (2016) 30-38).

The search for effective combat against tick infestation in bovines is being carried out by different control methods, such as the chemical control (chemical compounds, such as arsenicals, organochlorines, formamidines, cyclomidines, pyrethroids, etc.) alternative control (natural predators, homeopathic products, pastures that would make it difficult for the larvae to climb, etc.) and immunologic control, which covers the use of different types of vaccines.

In particular, the technology on antigen vaccines against bovine ticks has been studied since the mid-90s, same time as the development and registration of the only commercially available vaccines against ectoparasites for the control of infestations by bovine ticks. The vaccine that is currently commercialized for this purpose, which contains the protein that is the homolog of the protein Bm86, presents variations in efficacy in the different geographic locations.

In this connection, Almazen et al. (ALMAZAN, C. et al. Identification and characterization of *Rhipicephalus* (*Boophilus*) *microplus* candidate protective antigens for the control of cattle tick infestations. *Parasitol Res.* 106:471-479 (2010)) affirm that the recombinant antigen Bm86 of *Rhipicephalus* (*Boophilus*) *microplus* demonstrated protecting cattle against tick infestations. However, the variable efficacy of the vaccines based on Bm86 against geographic strains of ticks encouraged the development of research that seeks additional antigens for tick protection, to identify alternatives to the protein Bm86.

Some of these studies propose the use of complete proteins as antigens, such as trypsin inhibitors, subolesin, akirin, kallikrein, elastase inhibitors and peptides designed by reverse vaccinology in subsequent genomic studies.

Other lines of research propose the combination of antigens to obtain improved results in terms of efficacy in tick combat, considering that, in case a mechanism does not work or works in a less effective way, another mechanism can be duly efficient and exterminate the ticks by causing irreversible damage to some of their vital metabolic functions.

Despite the increase in the scientific knowledge about the role of these proteins in the control of bovine ticks, the alternative approaches to Bm86 described up to now have not shown to be promising enough for the manufacture of a commercial product, thus, improved strategies, more efficient and/or immunization agents, particularly for large scale vaccination, are still necessary.

Consequently, there still exists the need for a more efficient vaccine against ticks in mammal animals, particularly bovine cattle for the control of ticks of the species *Rhipicephalus* (*Boophilus*) *microplus*. Therefore, it is an objective of the present invention to overcome the disadvantages of the state of the art and supply this need by providing a peptide combination and composition able to reach unexpected and efficient results against tick infestation.

BRIEF DESCRIPTION OF SEQUENCES

The biologic sequences used for the development of the present invention, are described in the section Sequence Listing.

SEQ ID NO: 1 relates to an artificial sequence that is similar to a peptide fragment which function is related to the formation of the insect cuticle protein. Presents 73% sequence identity with *L. scapularis.*

SEQ ID NO: 2 relates to an artificial sequence that is similar to a peptide fragment which function is related to the formation of the insect cuticle protein. Presents 67% sequence identity with *L. scapularis.*

SEQ ID NO: 3 relates to an artificial sequence that is similar to a peptide fragment which function is related to the formation of the embryo.

Presents 88% sequence identity with *L. scapularis.*

SEQ ID NO: 4 relates to an artificial sequence that is similar to a peptide fragment which function is related to the formation of the embryonated eggs. Presents 70% sequence identity with *L. scapularis.*

SEQ ID NO: 5 relates to an artificial sequence that is similar to a peptide fragment which function is related to the formation of the embryonated eggs. Presents 55% sequence identity with *L. scapularis.*

SEQ ID NO: 6 relates to an artificial sequence that is similar to a peptide fragment which function is related to the mechanisms of signal transduction (TPR). Presents 90% sequence identity with *L. scapularis.*

SEQ ID NO: 7 relates to an artificial sequence that is similar to a peptide fragment which function is related to the formation of the zinc-dependent metalloprotease. Presents 30% sequence identity with *R. microplus.*

SEQ ID NO: 8 relates to an artificial sequence that is similar to a peptide fragment which function is related to the kazal-type serine protease inhibitor. Presents 45% sequence identity with *L. scapularis.*

SEQ ID NO: 9 relates to an artificial sequence that is similar to a peptide fragment which function is related to the chitin connection. Presents 67% sequence identity with *L. scapularis.*

SEQ ID NO: 10 relates to an artificial sequence that is similar to a peptide fragment which function is related to the trypsin inhibitor domain (Kunitz). Presents 43% sequence identity with *R. microplus.*

SEQ ID NO: 11 relates to an artificial sequence that is similar to a peptide fragment which function is related to the trypsin inhibitor (BPTI)—Kunitz. Presents 43% sequence identity with *R. microplus.*

SEQ ID NO: 12 relates to an artificial sequence that is similar to a peptide fragment which function is related to the saliva molecules that modulate host response. Presents 35% sequence identity with *L. scapularis.*

SUMMARY OF THE INVENTION

The present invention aims at solving the inconveniences of the state of the art cited above by means of new peptide combinations that are able to present satisfactory immunogenic response against ticks in mammals, particularly bovine cattle, particularly ticks of the species *Rhipicephalus microplus*. The new combinations of specific peptides of the present invention are able to reach greater technical advantages as regards the suppression of the vital metabolic functions of the referred ticks.

Thus, in a first aspect, the present invention refers to a combination of at least 2 immunogenic peptides selected from the group consisting in the peptides of SEQ ID NO: 1 to 12.

In a second aspect, the present invention refers to a chimeric peptide comprising combinations of at least 2 immunogenic peptides selected from the group consisting in the peptides of SEQ ID NO:1 to SEQ ID NO: 12, connected to each other by any means known to the state of the art.

In a third aspect, the present invention refers to an immunogenic composition comprising the combination of peptides or the chimeric peptide of the present invention and pharmaceutically acceptable excipients.

The present invention further refers to the use of the combination of peptides, the chimeric peptide or the composition described herein, to immunize, treat, protect, attenuate and/or prevent tick infestations in a mammal animal, particularly bovine cattle.

In a further aspect, the present invention refers to a method to induce immune response in mammal animals, particularly bovine cattle, wherein the method comprises obtaining the composition containing the chimeric peptide or the immunogenic composition herein described the administration thereof to an animal in need thereof and monitoring of the degree of tick infestation in the referred animal.

In a further aspect, the present invention refers to a kit, comprising the peptide combination, the chimeric peptide or the immunogenic composition, as defined by the present invention. Preferably, the kits are for vaccination.

Any of the objects and processes described above can serve as basis to compose the other objects and the preferred embodiments thereof, even in case said relation(s) has(have) not been explicitly described.

BRIEF DESCRIPTION OF THE FIGURES

In FIG. 5 we can observe the IgG production in groups 1 and 2 which corresponds to the immune response of the animals in face of the peptide stimulation. The results were observed in the ELISA method.

DETAILED DESCRIPTION OF THE INVENTION

Figure 1:
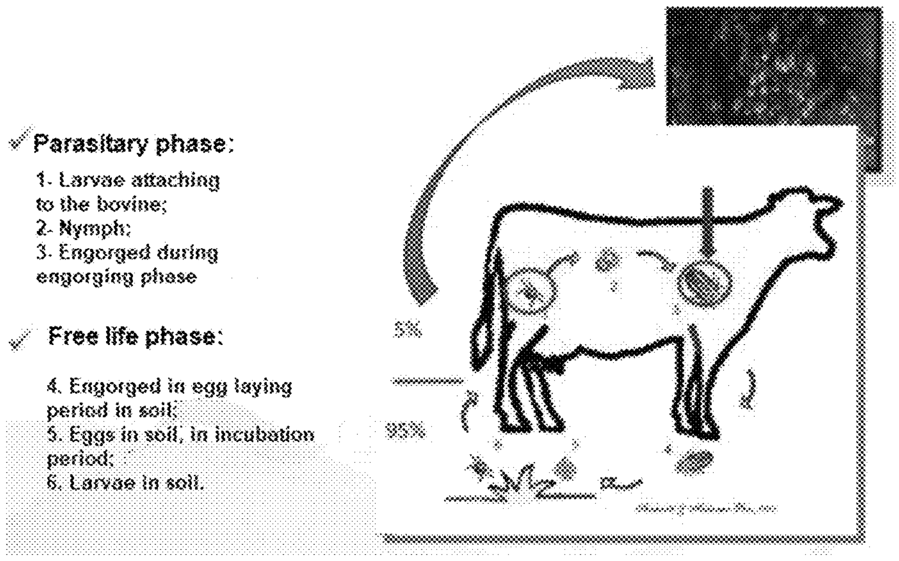
FIG. 1 illustrates, as state of the art, the biological cycle of the cattle tick.

Unless otherwise defined, all the technical expressions, annotations and other scientific terminology used herein are destined to comprise the meanings usually understood by those skilled in the field of the present invention. In some cases, the expressions with commonly understood meanings are defined in the present document with the purpose of bringing clearness and/or for ready reference, and the inclusion of said definitions in the present document must not be interpreted, necessarily, as representing a substantial difference in relation to what is generally understood in the state of the art.

The techniques and procedures described herein or referred by the present document are usually well understood and employed using the conventional methodology by those skilled in the art. As appropriate, the processes involving the use of kits and commercially available reagents are usually carried out in accordance with protocols and/or parameters defined by the manufacturer, save when otherwise indicated.

It must be emphasized that the present invention, where appropriate, is not limited to the methodology, protocols, cell lines, genus or species of animals, constructions and specific reagents described, which, in an obvious manner, can vary. Additionally, the terminology used in the present document has only the purpose of describing examples of specific embodiments and is not destined to limit the scope of the present invention.

Throughout this document, the single forms “one” and “the”, or single forms of any expression or term, include the references to the plural, unless the context clearly informs otherwise.

Throughout this document, the expression “comprises”, and any variations such as “the comprise” or “comprising”, must be interpreted as being “open expressions” able to imply the inclusion of additional elements or groups of elements, which were not explicitly described, not having limiting character.

Throughout this document, the expression "consists", and any variations such as "consist" or "consisting", must be interpreted as "closed expressions", not implying the inclusion of additional elements or groups of elements, which were not explicitly described, having limiting character.

Throughout this document, the exact values or ranges of exact values provided in relation to a factor, quantity, concentration or particular preference must be interpreted as also providing approximate values or ranges of values, such as by means of the expression "around".

Throughout this document, words and expressions such as "preferably", "particularly", "as", "such as", "more particularly" and similar, and variations thereof, must be interpreted as being entirely optional characteristics, preferred embodiments or possible non-exhaustive examples, without conferring scope limiting character.

Throughout this document, all the tiles and subtitles are used solely for convenience and must not be interpreted as being limitations of the present invention.

Throughout this document, the word "peptide", must be interpreted as being a single linear chain of monomer amino acids linked by peptide bonds. Amino acids which have been incorporated in peptides are called "residues". Every peptide has an N-terminal residue and a C-terminal residue in the corresponding extremities of the peptide. Further, throughout this document, the word "peptide" must be interpreted as comprising any number of consecutive residues. Further, the expressions "peptide", "polypeptide" and "protein" must be interpreted as synonyms, being interchangeable with each other and must not be interpreted as having a determined number of residues.

Throughout this document, the expression "chimeric peptide" must be interpreted as a peptide originating from the junction, bond, union or connection of two or more equal or different peptide fragments, as defined by the present invention, in any order, wherein said junction, bond, union or connection between peptide fragments can be performed by any means known to the state of the art. In a preferred embodiment, said junction, bond, union or connection between the peptide fragments is performed by a spacer. The peptide-spacer link is preferably performed by means of a peptide bond.

Further, throughout this document, the expressions "peptide", "chimeric peptide", "polypeptide", "peptide fragment" and "protein" must be interpreted as having any shape, being linear or having native three-dimensional structure or of particular interest. The peptide fragments to be bonded may originate from microorganisms of the same species or different species. Further, the peptide fragments and the chimeric peptides can be synthetically obtained (for example, by solid phase synthesis techniques), originated in recombinant form (for example, by means of use of expression cassette under the control of a specific promoter) or from any pertinent technologies of the field of the invention known by a person skilled in the art. Sufficient techniques for guidance are also found in the literature.

According to the present invention, structural modifications to improve the stability in vivo of the peptides, as well as improve the molecular properties related to the action mechanism, resulting in improvement of the pharmacologic activity (peptidemimetics), if any, must be considered as within the scope of the present invention.

Said modifications can be limited specifically to protect or replace the labile bond (peptide bond), from the introduction of fragments/atypical portions (non-peptide), or even alter the peptide conformation. Promising molecular modifications (non-peptide) would be those that attempt to mimetize the structure and molecular properties of the peptide.

Examples of possible molecular modifications would be: pseudopeptides, which present structural modifications in the main chain of at least one peptide bond with isoster groups or iso-electronic, such as reduced amides, azopeptides, retro-inverse peptides, peptoids; replacement with unnatural amino acids, such as replacement of L-amino acids with respective D-enantiomers; use of N-alkyl amino acids, alpha-amino acids, alpha-substituted, alpha amino acids beta-substituted, proline analogues, gama- and beta-amino acids; ether bridges, biaryl, disulfide or others that mimetize those already cited; N and C terminal connection with lateral chains of amino acids (Gentilucci, L., De Marco, R., Cerisoli, L. Chemical Modifications Designed to Improve Peptide Stability: Incorporation of Non-Natural Amino Acids, Pseudo-Peptide Bonds, and Cyclization. *Current Pharmaceutical Design*, v. 16, p. 3185-3203, 2010).

Additionally, a person skilled in the art would recognize that, conservative replacements that result in alteration of an amino acid by another chemically similar amino acid in a sequence, are within the scope of the present invention. Said conservative substitutions providing similarly functional amino acids are known in the art.

In one embodiment, the present invention refers to a combination of at least 2 immunogenic peptides selected from the group consisting in the peptides of SEQ ID NO: 1 to 12.

In an additional embodiment, the present invention refers to a chimeric peptide comprising combinations of at least 2 immunogenic peptides selected from the group consisting in the peptides of SEQ ID NO:1 to SEQ ID NO: 12. The peptide fragments in the chimeric peptide can be linked to each other by any means known to the state of the art. In a preferred embodiment, said peptide fragments are linked to each other by means of a spacer.

The expression "peptide combination" must be interpreted as being a grouping, collection or aggregate comprising at least two peptides of SEQ ID NO:1 to 12 as defined in the present invention. In this context, the expression "at least two" refers to the quantity from 2 to 24 peptides, as well as any range between said values. Preferably, the peptide combination, according to the present invention, comprises from 2 to 8 peptides, preferably from 3 to 7 peptides, more preferably from 4 to 6 peptides.

In a preferred embodiment, the combination or the chimeric peptide of the present invention comprises 6 peptides selected from the group consisting in the peptides of SEQ ID NO: 1 to 12. In particular, the combination or the chimeric peptide of the present invention comprises the peptides of SEQ ID NOs: 1 to 6 or the peptides of SEQ ID NOs: 7 to 12.

As previously pointed out, the peptide fragments that compose the chimeric peptide, object of the present invention, can be linked to each other by any means or way known to the state of the art. In a preferred embodiment, said fragments are linked to each other by means of a spacer. In this context, as previously pointed out, "spacer" must be interpreted as being a junction, bond, union or connection of the peptides, as defined in the present invention. For example, the spacer may be constituted by one or more glycine residues (Gly or G) or one or more proline residues (Pro or P) or any combinations thereof. For example, the spacer can be GPGPG. Preferably, the spacer is constituted by one or more glycine residues. More preferably, the spacer is constituted by 2 to 15 glycine residues, particularly 2 to 10 glycine residues, more particularly 3 to 5 glycine residues. Said glycine residues were selected to confer conformation freedom (flexibility) to the resulting hybrid peptide, without compromising the action predicted to a great extent. Thus, the nature of the spacer is not particularly relevant or critical for the present invention. In this sense, it must be understood, according to the present invention that any spacer that grants an equivalent function to the resulting chimeric peptide, is within the scope of the present invention.

In another embodiment, the present invention refers to an immunogenic composition comprising the peptide combination or the chimeric peptide of the present invention and pharmaceutically acceptable excipients, in therapeutically efficient amounts.

The expression "pharmaceutically acceptable excipient" must be interpreted as being any vehicle, or substance which is not a pharmaceutically active ingredient. Therefore, it must be understood, according to the present invention, that any conventional pharmaceutically acceptable excipient, in any form, usually employed to act as excipient, is within the scope of the present invention. Pharmaceutically acceptable excipients are duly known by those skilled in the art, and they may be chosen from *Remington: The Science and Practice of Pharmacy*, Remington, 22$^{nd}$ edition or Handbook of pharmaceutical excipients, Rowe, 8$^{th}$ edition, herein incorporated as reference. The pharmaceutically acceptable excipient includes but is not limited to: buffer or saline solution, stabilizer, surfactant, solubilizer, diluents, carriers, emulsifier and preservative.

Preferably, the excipient is added in an amount from around 1 to 3 ml per dose. More preferably, 2 ml per dose.

Throughout the present document, the expression "diluent" must be interpreted as being any substance having the function of diluting, conserving the properties of what is being diluted. Therefore, it must be understood, according to the present invention, that any conventional diluent, in any form, usually employed to dilute, is within the scope of the present invention. Acceptable diluents are duly known by a person skilled in the art. The diluent includes, but is not limited to: water, alcohol and sterile solutions.

Throughout the present document, the expression "adjuvant" must be interpreted as being any substance that modulates or increases the immunogenicity of the peptides of the present invention. Therefore, it must be understood, according to the present invention, that any conventional adjuvant, in any form, usually employed in compositions with this purpose, is within the scope of the present invention. The adjuvant includes, but its not limited to: Montanide®, Freund complete adjuvant, Freund incomplete adjuvant, aluminum hydroxide, aluminum phosphate, silica and saponin.

Throughout the present document, the expression "carrier" must be interpreted as being a transporter, permease, or any structure wherein the peptide can be incorporated or with which it may be associated, to guide and/or ease and/or improve the triggering of an immune response by a human being or an animal. Therefore, it must be understood, according to the present invention, that any conventional carried, in any form, usually employed to act as carrier is within the scope of the present invention. The carrier includes but is not limited to: any inert heterologous substance, KLH, horse albumin, colloidal gold particles, antibodies or fragments of antibodies, polymers, vesicles and nanovesicles.

By "stabilizer agents" it must be understood, but not limited to, saccharides, trehalose, and mannitol, sucrose and similar, to increase and/or maintain the shelf life of the product and/or to enhance the stability, or combinations thereof.

In a preferred embodiment, the composition of the present invention can further comprise an additional biologically active substance or compound.

Throughout the present document, the expression "additional biologically active substance or compound" must be understood as being any substance or compound that exerts a biologically active effect. Therefore, it must be understood, according to the present invention, that any additional biologically active substance or compound, in any form, usually employed to act as such, is within the scope of the present invention. They can exert their function by the same mechanism or by different or similar mechanisms. They can have a multiplicity of related action mechanisms and/or have independent action mechanisms. The additional biologically active substances or compounds include, but are not limited to: enhancers, agonists, etc.

Throughout the present document, the expression "therapeutically effective amount" refers to the quantity of peptide that suffices to result in a therapeutic effect in the animal. The therapeutically effective amount can be promptly determined by a person skilled in the art following routine procedures, without undue experimentation, considering the route of administration, the specific composition used, the clinical factors, the age and weight of the human or animal, among others, if that is the case, as to be independent of the cited factors. Preferably, the therapeutically efficient amount is from 50 to 500 μg, more preferably from 100 to 300 μg, more preferably of 200 μg.

The composition of the present invention can be formulated according to the standard methodology known by a person skilled in the art, not being particularly relevant to the present invention. Further, the composition of the present invention can be in any form, considering the function of the composition, the route of administration, and the desired effect. Possible forms include, but are not limited to: solution, mixture, powder, granules, aerosol, or freeze dried.

The composition of the present invention can be administered to the animal by various standard routes of administration, considering the form of the composition and the desired effect. It can be for a mainly local effect, or systemic. The composition of the present invention can, for example, be in the form of a solution for subcutaneous administration, in aerosol form for intra-nasal administration or even in the form of a solution for intramuscular administration, for example, in the neck plate region. Other routes of administration include, but are not limited to: oral, topical, implantable, intravenous, intra-arterial, intradermal, intra-peritoneal and parenteral.

The composition of the present invention is preferably a vaccine. Preferably, the composition form of the vaccine of the present invention is a solution, for subcutaneous administration.

By "immunogenic composition" it must be understood that it relates to a composition comprising at least one antigen that provokes an immunologic response in the host of an immune cell response and/or mediated by host to immunogenic composition or applied vaccine. Preferably, the host will exhibit a therapeutic or protective immunologic response, so that the resistance to a new infestation will be improved and/or the clinical severity of the disease will be reduced.

The expression "vaccine" is destined to the use of an immunologically effective amount of one or more immunogenic compound(s) and a pharmaceutically acceptable vehicle. The immunogenic compounds for the present invention are the peptides of SEQ ID NO: 1 to SEQ ID NO: 12.

The composition of the present invention is preferably for immunizing, treating, protecting, attenuating and/or preventing tick infestation in mammal animals, particularly bovine cattle animals. In a preferred embodiment, the tick is *Rhipicephalus microplus.*

The antigenic composition or vaccine described herein can be administered in the most appropriate or necessary dose to provide an immune response of interest in the animal, particularly the bovine.

In one embodiment, the present invention refers to the use of peptide combinations, of the chimeric peptide, or the composition described herein, to prepare a composition or medication to immunize, treat, protect, attenuate and/or prevent tick infestations in mammal animals, particularly bovine cattle animals, by means of the immunization of these animals.

In one embodiment, the peptide combination, chimeric peptide or immunogenic composition is administered to the animals in a concentration from 50 to 500 μg, more preferably from 100 to 300 μg, even more preferably of 200 μg. In a preferred embodiment, there are administered 3 doses in an interval varying from 10 to 30 days, preferably 21 days.

The "sequence identity" as it is known in the state of the art, refers to a relation between two or more sequences of polypeptides or two or more sequences of polynucleotides, that is, a reference sequence and a sequence given to be compared with the reference sequence. The identity of the sequence is determined comparing the given sequence to the reference sequence after the sequences have been ideally aligned to produce the highest level of similarity of sequence, as determined by the correspondence between character chains of said sequences. During said alignment, the sequence identity is determined on a position-by-position basis, for example, the sequences are "identical" in a particular position if in this position the nucleotides or amino acid residues are identical.

The total number of said position identities is, subsequently, divided by the total number of nucleotides or residues in the reference sequence to provide % of sequence identity.

The sequence identity can be easily calculated by known methods, including, but not limited to those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Partl, Griffin, A. M. e Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H. and Lipman, D., SIAM J. Applied Math., 48: 1073 (1988), the teachings of which are herein incorporated by reference.

Preferred methods to determine the sequence identity are designated to provide the highest correspondence between the tested sequences. Methods for determining the sequence identity are encoded in publicly available computer programs that determine the sequence identity between given sequences. Examples of said programs includes but are not limited to the program packet GCG (Devereux, J., et al., Nucleic Acids Research, 12(1):387 (1984)), BLASTP, BLASTN e FASTA (Altschul, S. F. et al., J. Molec. Biol., 215:403-410 (1990). The BLASTX program is publicly available at NCBI and other sources (BLAST Manual, Altschul, S. et al., NCVI NLM NIH Bethesda, MD 20894, Altschul, S. F. et al., J. Molec. Biol., 215:403-410 (1990), the teachings of which are herein incorporated by reference. These programs ideally align sequences using standard interval weights to produce the highest level of sequence identity between the given and reference sequences.

A person skilled in the art knows that the composition and the vaccine described herein can incorporate sterile injectable, physiologically acceptable known solutions.

In an additional embodiment, the present invention refers to a method to induce an immune response in mammal animals, particularly bovine cattle, wherein the method comprises the step of administering a therapeutically effective amount of the peptide combination, of the chimeric peptide or the immunogenic composition described herein, to an animal in need thereof In an additional embodiment, the present invention refers to a kit, comprising the peptide combination, the chimeric peptide or the immunogenic composition, as defined by the present invention and instructions for use. Preferably, the kits are for vaccination.

the present invention is further illustrated by the following examples which, however, must not be interpreted as being limitations to the scope of the invention. The characteristics described in the above specification and in the following examples can, separately and in any combination, serve as basis for the execution of the present invention in its various forms of embodiment and possible execution.

EXAMPLES

Example 1. Immune Response Induction in Bovines and Evaluation of Degree of Tick Infestation The proposal of the present invention has the purpose of evaluating the immunoprotection of peptides selected in immunized bovine cattle and, subsequently, challenged by means of artificial infestation with larvae of *R. microplus* ticks. The peptides used were divided in groups, as follows:

Group 1: peptides of SEQ ID NO: 1 to 6; and

Group 2: peptides of SEQ ID NO: 7 to 12.

The weaned animals of the Angus breed, with average weight around 250 kg, were grouped in number of 5 animals each, and submitted to vaccine stimulation using 200 μg of peptides designed and associated to the KLH carrier, apart from being solubilized in adjuvant Montanide®.

The control group received only the inoculation of the adjuvant and saline solution in the same volume for the dose.

Each animal was stimulated with three doses, subcutaneously administered, in a volume of 2 mL, in an interval of 21 days and, subsequently, submitted to the challenge with 15.000 larvae of the *Rhipichephalus microplus* tick, 21 days after the last inoculation.

After the collection of the ticks in the individual stalls, there were obtained the results of the infestation and performed the incubation of these to know their biological performance. The data were compared with the control group.

The animals were monitored regarding the clinical aspects without presenting alterations in the body temperature, feeding behavior and reaction at the place of the vaccine inoculation.

Figure 2:
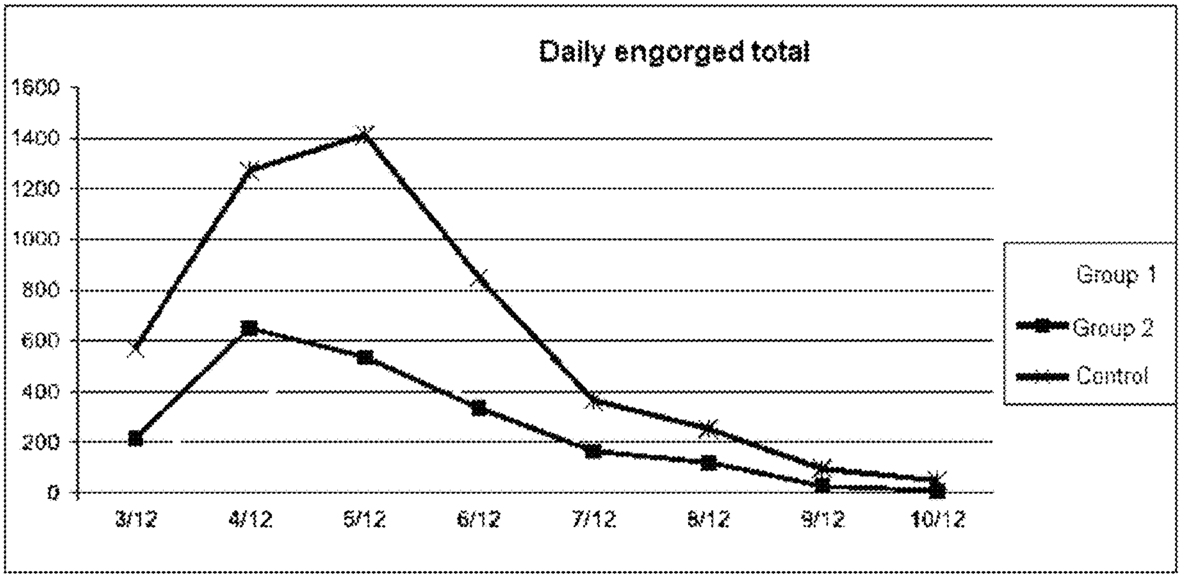
FIG. 2 illustrates the graph with the average amount of ticks (engorged) collected daily by group during the tick drop period in the infested animals.
Figure 3:
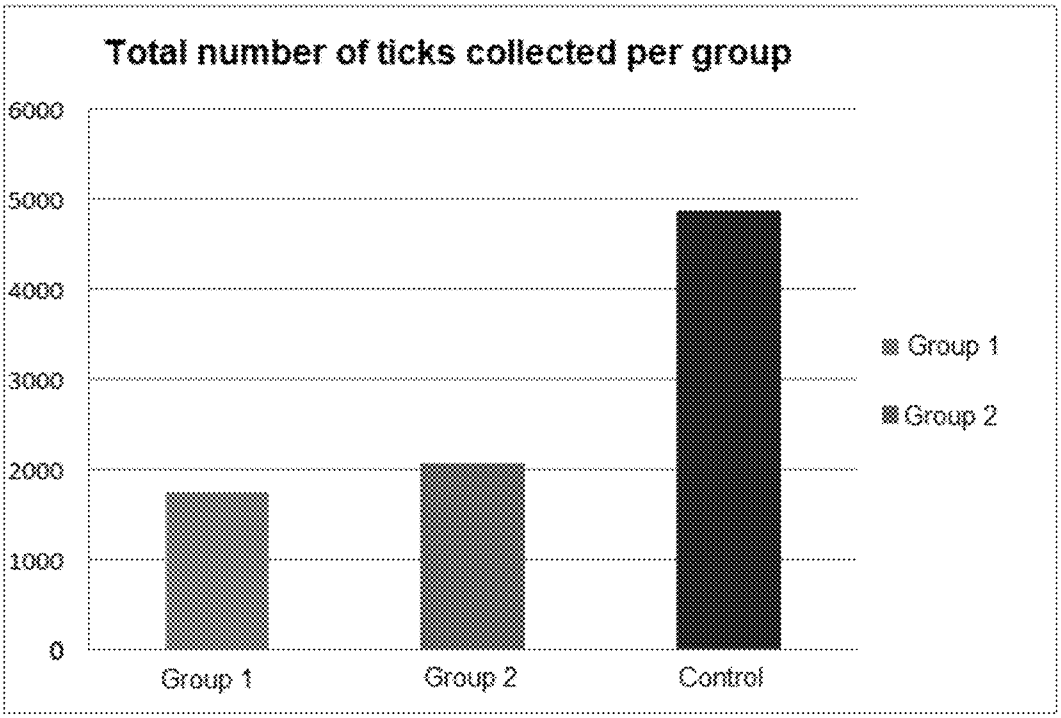
FIG. 3 illustrates the total number of ticks collected in the groups tested after the challenge.

Thus, when carrying out the collection of ticks in the individual stalls, there were obtained results of the degree of infestation and subsequently of the tick incubation, compared with the control group, without vaccine. FIG. 2 shows the average amount of ticks (engorged) collected daily by group, along the period of tick loss in the infested animals. The total number of ticks produced in groups 1 and 2 after the challenge is illustrated in FIG. 3.

Figure 4:
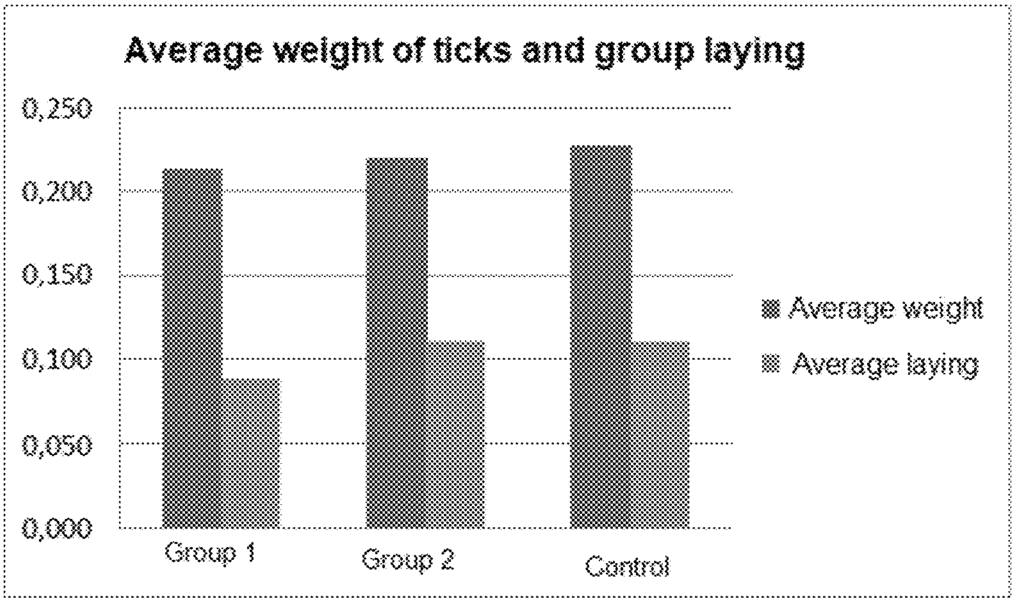
FIG. 4 illustrates the average weight of the ticks (engorged) and the respective laying per group.

At the laboratory the average weight of the engorged females—engorged—collected daily during the experiment and the respective weight of the egg production, shown in FIG. 4.

Figure 5:
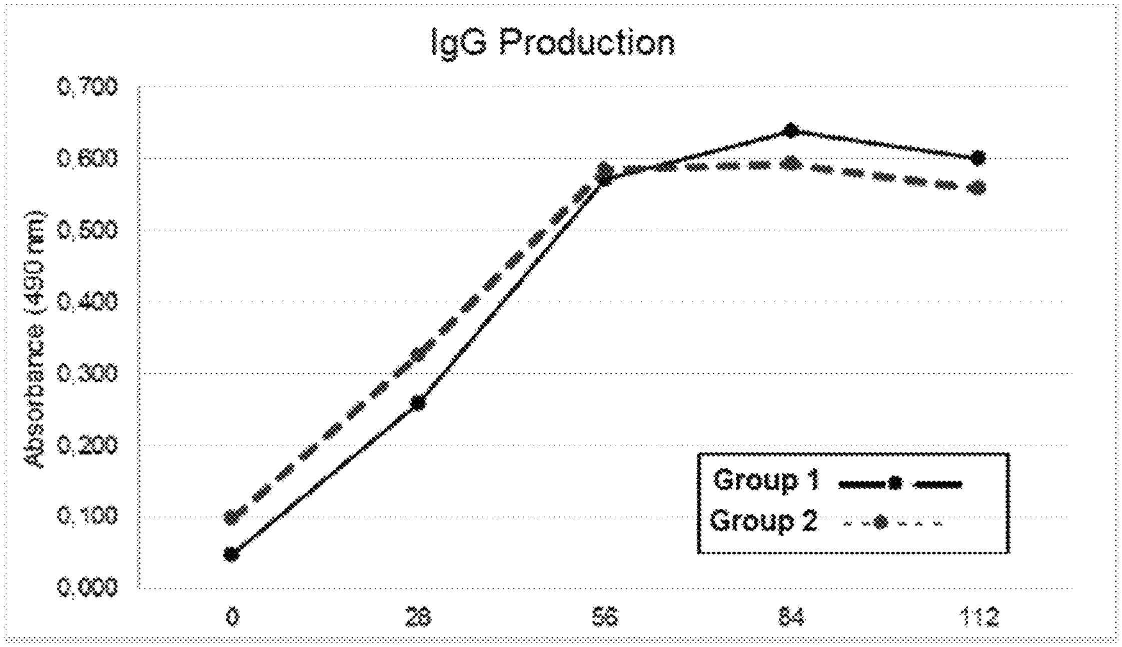
FIG. 5 illustrates the average immune response (IgG) of the animals vaccinated with peptides in the groups tested. All the egg samples were incubated until hatched and the hatchability rate was evaluated in the groups for the purposes of calculation of the efficacy of the immunoprotection of the bovines.

All the samples of the egg mass were incubated until the hatching of the larvae. Subsequently, the hatchability rate was evaluated for the purposes of calculation of the efficacy of the immunoprotection of the bovines. In FIG. 5 we can observe the production of IgG in groups 1 and 2 which corresponds to the immune response of the animals in face of the peptide stimulation. The results were observed in the ELISA method.

Example 2. Evaluation Regarding Vaccine Efficacy

The calculation of the efficacy involved the following parameters:

Number of ticks;
Weight of engorged ticks;
Weight of the eggs; and
Hatchability

For the calculation of the efficacy the following formula was used:

$$Ef=100\times[1-(NET\times EW\times EF\times EC)]$$

In the above formula we have:

NET=total number of ticks of the immunized group/total number of ticks of the control group;

EW=(egg weight/number immunized ticks)/(egg weight/number control ticks);

EF=(egg weight/weight immunized ticks)/(egg weight/weight control ticks); and

EC=% hatchability immunized larvae/% control hatchability.

The efficacy percentages, in comparative terms, were obtain according to the data and table below:

Group 1: NET=0.3600; EW=0.8489; EF=0.9809; and EC=1.0282.

Group 2: NET=0.4221; EW=1.0372; EF=1.0861; and EC=

| Groups | Efficacy |
|---|---|
| 1 | 69 |
| 2 | 51 |

As can be observed, both Groups 1 and 2 presented very satisfactory results, and higher than the results observed in the state of the art

The invention claimed is:

1. A peptide combination comprising at least two immunogenic peptides having different amino acid sequences, wherein each of the at least two immunogenic peptides consists of an amino acid sequence selected from SEQ ID NOs: 1-12.

2. The peptide combination according to claim 1, wherein the peptide combination comprises six immunogenic peptides having different amino acid sequences, wherein each of the six immunogenic peptides consists of an amino acid sequence selected from SEQ ID NOs: 1-12.

3. The peptide combination according to claim 2, wherein the six immunogenic peptides consist of the amino acid sequences of SEQ ID NOs: 1-6.

4. The peptide combination according to claim 2, wherein the six immunogenic peptides consist of the amino acid sequences of SEQ ID NOs: 7-12.

5. A chimeric peptide comprising at least two immunogenic peptide sequences, each consisting of an amino acid sequence selected from SEQ ID NOs: 1-12, wherein the at least two immunogenic peptide sequences are linked by one or more peptide bonds, optionally via a spacer.

6. The chimeric peptide according to claim 5, wherein the chimeric peptide comprises six immunogenic peptide sequences, wherein each of the six amino acid sequences consists of an amino acid sequence selected from SEQ ID NOs: 1-12.

7. The chimeric peptide according to claim 6, wherein the six immunogenic peptide sequences consists of the amino acid sequences of SEQ ID NOs: 1-6.

8. The chimeric peptide according to claim 6, wherein the six immunogenic peptide sequences consists of the amino acid sequences of SEQ ID NOs: 7-12.

9. An immunogenic composition comprising a pharmaceutically acceptable excipient and:

(a) a peptide combination comprising at least two immunogenic peptides having different amino acid sequences, wherein each of the at least two immunogenic peptides consists of an amino acid sequence selected from SEQ ID NOs: 1-12; or (b) a chimeric peptide comprising at least two immunogenic peptide sequences, each consisting of an amino acid sequence selected from SEQ ID NOs: 1-12, wherein the at least two immunogenic peptide sequences are linked by one or more peptide bonds, optionally via a spacer.

10. The immunogenic composition according to claim 9, further comprising an additional biologically active compound.

11. The immunogenic composition according to claim 9, wherein the immunogenic composition is a solution, a mixture, a powder, granules, an aerosol, or freeze dried.

12. The immunogenic composition according to claim 9, wherein the immunogenic composition is a vaccine.

13. A method for inducing an immune response comprising:

(a) obtaining an immunogenic composition according to claim 9;

(b) administering the immunogenic composition to an animal; and (c) monitoring the degree of tick infestation in the animal.

14. The method according to claim 13, wherein the immunogenic composition is a vaccine.

15. The method according to claim 13, wherein the method induces an immune response for immunizing, treating, and/or protecting against tick infestations in a mammal.

16. A kit comprising the immunogenic composition according to claim 9 and instructions for use.

17. The kit according to claim 16, wherein the immunogenic composition is a vaccine.

* * * * *